(12) United States Patent
Guy

(10) Patent No.: US 9,877,813 B2
(45) Date of Patent: Jan. 30, 2018

(54) DENTAL DEVICE MATERIAL PREPARATION

(76) Inventor: Frederick Ralph Guy, Syracuse, NY (US)

( * ) Notice: Subject to any disclaimer, the term of this patent is extended or adjusted under 35 U.S.C. 154(b) by 1709 days.

(21) Appl. No.: 13/341,584

(22) Filed: Dec. 30, 2011

(65) Prior Publication Data

US 2012/0171640 A1    Jul. 5, 2012

Related U.S. Application Data

(60) Provisional application No. 61/428,259, filed on Dec. 30, 2010.

(51) Int. Cl.
| | |
|---|---|
| *A61C 13/08* | (2006.01) |
| *A61C 13/00* | (2006.01) |
| *G06Q 50/22* | (2012.01) |
| *A61C 5/77* | (2017.01) |

(52) U.S. Cl.
CPC ............ *A61C 13/0022* (2013.01); *A61C 5/77* (2017.02); *A61C 13/08* (2013.01); *G06Q 50/22* (2013.01); *Y10T 409/303752* (2015.01)

(58) Field of Classification Search
None
See application file for complete search history.

(56) References Cited

U.S. PATENT DOCUMENTS

| | | | |
|---|---|---|---|
| 4,693,986 A | 9/1987 | Vit et al. | |
| 4,937,928 A | 3/1990 | Van Der Zel | |
| 5,378,154 A | 1/1995 | Van Der Zel | |
| 5,871,800 A * | 2/1999 | George | A23N 5/002 426/489 |
| 7,708,557 B2 | 5/2010 | Rubbert | |
| 2002/0102520 A1* | 8/2002 | Iiyama | A61C 13/0004 433/215 |
| 2006/0210494 A1* | 9/2006 | Rabiei | A61C 8/0012 424/57 |
| 2013/0224684 A1 | 8/2013 | Guy | |

FOREIGN PATENT DOCUMENTS

| | | |
|---|---|---|
| EP | 1097692 A2 | 5/2001 |
| KR | 1020060054668 | 5/2006 |
| KR | 1020110056594 | 5/2011 |

OTHER PUBLICATIONS

Hunger, Fred J., Tagua: The Vegetable Ivory Substitute, from Lathes and Turning Techniques, The Best of Fine Woodworking Magazine (Jul./Aug. 1990). p. 65-67.*

Ryu, J., Ku, S.H., Lee, H., Park, C.B., Mussel-Inspired Polydopamine Coating as a Universal Route to Hydroxyapatite Crystallization, Advanced Functional Material, 2010, 20, 2132-2139, www.afm-journal.de.*

(Continued)

*Primary Examiner* — Christina Johnson
*Assistant Examiner* — Mohammad M Ameen
(74) *Attorney, Agent, or Firm* — Medley, Behrens & Lewis, LLC

(57) ABSTRACT

A method of preparing organic and natural material for making teeth and typical dental devices or appliances having sufficiently hard and durable chewing surfaces, obtained from sustainable resources.

15 Claims, 2 Drawing Sheets

(56) References Cited

OTHER PUBLICATIONS

Ryu, et al., "Mussel-Inspired Polydopamine Coating as a Universal Route to Hydroxyapatite Crystallization", In Advanced Functional Materials, vol. 20, 2010, pp. 2132-2139.
PCT International Search Authority, International Search Report and Written Opinion, PCT/US2011/060529, dated Jun. 19, 2012 (12 pages).
European Patent Office, "Communication Pursuant to Rules 70(2) and 70a(2) EPC for European Patent Application No. 11839111.9", dated Jun. 16, 2015, 10 pages.
European Patent Office, "Supplementary European Search Report for European Patent Application No. 11839111.9", dated May 19, 2015, 5 pages.
United States Patent and Trademark Office, "Decision on Reconsideration for U.S. Appl. No. 13/295,248", dated May 24, 2017, 9 pages.
United States Patent and Trademark Office, "Decision on Reconsideration for U.S. Appl. No. 13/295,248", dated Feb. 21, 2017, 11 pages.
United States Patent and Trademark Office, "Appeal Decision for U.S. Appl. No. 13/295,248", dated Sep. 28, 2016, 26 pages.
Eide, Heidi Marie, "Examiner's Response to Appeal Brief for U.S. Appl. No. 13/295,248", dated Jul. 11, 2014, 11 pages.
Eide, Heidi Marie, "Final Office Action for U.S. Appl. No. 13/295,248", dated Apr. 2, 2014, 17 pages.
W.P. Armstrong, "Vegetable Ivory", Noteworthy Plants, Jan. 1999, Retrieved At: <<http://waynesword.palomar.edu/pljan99.htm>>, 10 pages.
dictionary.com, "Denture", Retrieved At: <<http://www.dictionary.com/browse/denture>>, Retrieved Date: Jul. 17, 2017, 3 pages.
Neal, Phillip C., "Interesting Facts in the History of Dentures—Crystal Lake Dentist", Sep. 16, 2011, Retrieved At: <<http://drnealblog.blogspot.com/2011/09/interesting-facts-in-history-of.html>>, 6 pages.
Examiner Gisz, Xavier, "Patent Examination Report No. 1 for Australian Patent Application No. 2011325965", dated Nov. 18, 2014, 4 Pages.
"Artificial Teeth", Ann Arbor Argus, Dec. 13, 1895, Retrieved from: http://oldnews.aadl.org/node/135009, 2 Pages.
Eide, Heidi Marie, Non-Final Office Action in U.S. Appl. No. 13/295,248, dated Oct. 29, 2013 (14 pages).
Hunger, Fred, "Tagua: The Vegetable Ivory Substitute," Jul./Aug. 1990, pp. 65-67.
Janick, Jules and Paull, Robert E., "The Encyclopedia of Fruit & Nuts", CAB International, 2008, p. 152.

* cited by examiner

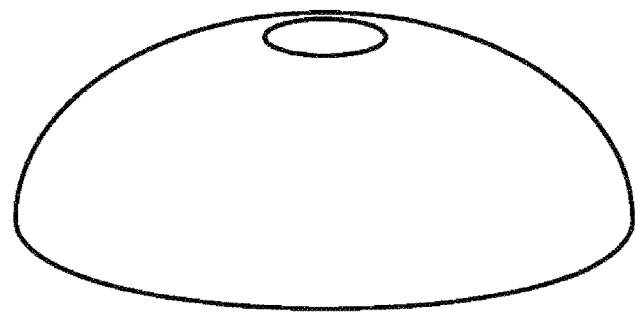
FIG. 3
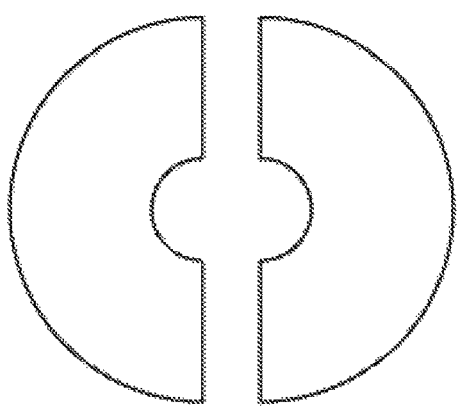 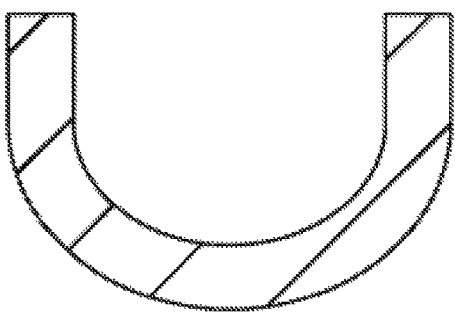
FIG. 4 FIG. 5

DENTAL DEVICE MATERIAL PREPARATION

This application claims priority to U.S. Provisional Patent Application Ser. No. 61/428,259, filed on Dec. 30, 2010, and entitled "Method of processing tagua nuts to pre-form material suitable for use in CNC milling machines and for fabrication of natural dental prostheses so that sustainable business practices are supported".

SUMMARY OF THE INVENTION

The present invention applies to preparing organic and natural material for making typical dental devices or appliances having sufficiently hard and durable chewing surfaces, obtained from sustainable resources. The natural material has physical characteristics providing durability, texture, color, and shading that match natural teeth necessary for utilitarian and cosmetically pleasing dental devices. The natural materials are sufficiently workable when using normal manufacturing techniques and equipment routinely applied for making currently available dental devices comprising non-natural or sustainable materials such as metal and ceramics.

BACKGROUND OF THE INVENTION

Humans and animals have natural teeth to assist in mastication of food and which are essential for sustaining good health. Teeth, however, comprise living tissue that may be corruptible by neglect, abuse and, or disease. In extreme cases decayed or damaged teeth are not reparable with typically available prophylaxis and must be extracted for the well-being of the patient. Notwithstanding removal, in the opinion of dental professionals, it is important that extracted teeth be replaced by prosthesis equipped with chewing surfaces. Replacements for teeth and the method for making such replacements are well known to those skilled in the art and include devices selected from the group consisting of bridges, full dentures, partial dentures, crowns, caps and combinations thereof.

The aforementioned dental devices are currently made from a number of materials that provide sufficient durability to sustain the rigors of chewing as well as provide good cosmetic aesthetics to match the remaining natural teeth in terms of physical factors including, but not necessarily limited to shape, size, texture, and color. Currently the materials used to make such devices include non-sustainable precious metals such as gold, ceramics, porcelain, plastics or composites of these materials. Standard dental devices are typically made of the above materials with a uniform high degree of hardness throughout the material, unlike natural teeth which consist of multiple layers of organic and mineral material in an ascending degree of hardness, from root to dentin to enamel, which has both formal and functional qualities and characteristics. Those qualities and characteristics are perfectly adapted to provide a kind of cushion or shock absorbing effect which protects the surrounding maxillofacial structure from stress induced damage. Such damage can include serious bone, muscular, and nerve damage, which is more likely to occur when superfluously hard and rigid dental prosthetics replace natural teeth which have a natural shock absorbing quality.

The present invention provides a natural, agriculturally derived solution that has substantially the same variable component hardness, and cushioning effect, as natural teeth.

Most dentists and dental patients have expressed high interest in prosthetic dental devices comprising natural, sustainable or "green" materials. Up to now, however no suitable natural and sustainable materials has been found to be a satisfactory in terms of the physical attributes previously mentioned. Therefore, there remains an unmet need for dental devices comprising a natural, sustainable material that achieves a satisfactory quality of hardness and durability.

BRIEF DESCRIPTION OF THE DRAWINGS

FIG. 3 is an exemplary illustration of endosperm of a tagua nut in a shape that conforms generally to the arc and slope of a patient's upper or lower set of natural teeth.

FIG. 4 is an exemplary illustration of a bored endosperm of a tagua nut that is cut in half and prepared for milling.

FIG. 5 is an exemplary illustration of a customized final dental prosthetic.

DETAILED DESCRIPTION OF THE INVENTION

A. Processes for Dental Device Material Preparation

In an embodiment of the invention, the dental devices comprise dehydrated and hardened endosperm of the nut of the Tagua palm, a species of the genus *Phytelephas*. *Phytelephas* is a genus containing six species of palms (family Arecaceae), occurring from southern Panama along the Andes to Ecuador, Bolivia and Peru. They are medium-sized to tall palms reaching 20 meters tall, with pinnate leaves. They are commonly known as ivory palms, ivory-nut palms, or Tagua palms; their scientific name means "plant elephant". This and the first two of the common names refer to the very hard white endosperm of their seeds (Tagua nuts), which resembles elephant ivory. In its original state, the "nut" is covered with pericarp. The nut is covered with a brown, flaky skin and shaped like a small avocado, roughly 4-8 cm in diameter. Since the nut has a protective husk or shell, once the nuts are harvested, there is no extreme inspection, sorting, and handling that must be taken to sort the nuts before processing. This material is harvested by the usual manual or machine harvesting methods generally known in the art.

The dehydrated Tagua nut material's texture, color, and shading vary over the range normally associated with natural teeth. To that end, the desired shading and color of the material is selected individually for the patient prior to manufacturing the device. Furthermore, the color of the material can be modified by routine method known in the art for bleaching material or foods such as wheat flour. Additionally, the texture of the material may be manipulated to create a consistent surface of the device that matches the natural teeth to avoid preoccupation by the patient's tongue.

B. Processing the Dental Device Material

Processing the dental device material derived from the Tagua nuts includes the steps of shelling, and curing the nuts by dehydration or desiccation. Dehydration or desiccation may be achieved wherein the nuts are dried at ambient conditions or accelerated using industrial equipment to rapidly drive off water to a desired level of dryness.

The present invention is directed at a sustainable method of doing business by leveraging the natural qualities of hardness, color, shape, and size of a plant material, as an alternative to artificial dental materials, so as to minimize the amount of energy used and reduce waste resulting from production. It is also directed at a method of processing dried endosperm of tagua nuts for use in CNC Milling Machines to make customized dental prostheses.

Figure 1:
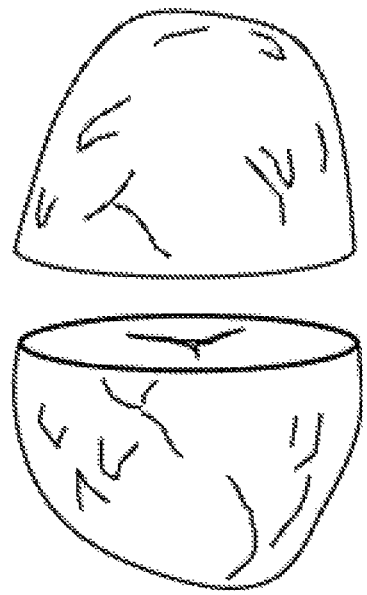
FIG. 1 is an exemplary illustration of a dehydrated and denuded tagua nut that has been cut into two hemispheres.
Figure 2:
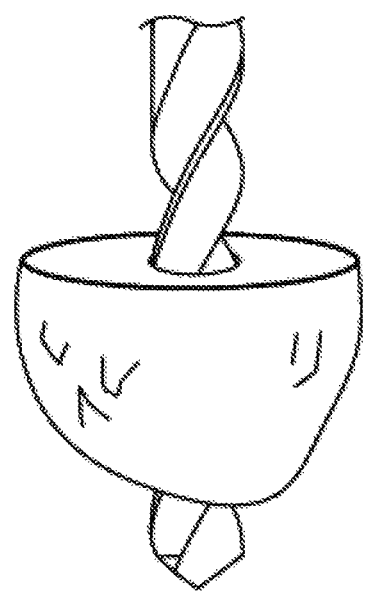
FIG. 2 is an exemplary illustration of making a boring in a hemisphere of a tagua nut.

In the preferred embodiment, a dehydrated tagua nut that has been denuded of the outer brown skin is cut into two hemispheres, as illustrated in FIG. 1. Cutting the nut in this way exposes the irregular shaped hollow center area which is surrounded by a hemisphere of endosperm that is suitable for milling as denture and crown material. The center empty core may be modified by a boring made at some angle vertical to the initial cut made at this step, as illustrated by FIG. 2. This boring renders the irregular jagged character of the hollow core of the nut smooth and uniform in surface quality. The boring is made to pass through the surface of the hemisphere such that a bowl shaped ring of endosperm is provided without crevices. In some instances the boring is done using a boring bit with a rounded top so that the hemisphere is not perforated. In that case, the boring step produces a bowl shaped piece of endosperm with an interior surface without crevices. Other shapes and degrees of preforming can be achieved alternatively as a given case may require. Alternate means of carving the endosperm to remove irregularities and to better conform the Tagua pieces to the human jaw and palette may be used. Mechanical, chemical, sonic, and photonic methods can be applied individually or in combination to modify the shapes and sizes required for use in milling devices. The cutting and shaping of the tagua nut as described may be done by computer assisted means.

By processing the nut in this way, the endosperm is rendered uniform in material quality and in a shape that conforms generally to the arc and slope of a patient's upper or lower set of natural teeth, as illustrated by FIG. 3.

As illustrated in FIG. 4, the ring or bowl is cut in half such that at least a part of an upper or lower denture can be milled from the resulting pieces with minimum processing and waste. A smaller segment of the bowl or ring can be cut out to provide material pre-cut for milling into a partial set of dentures or for a segment of a full set made of the smaller cuts in combination. A single cap or bridge can likewise be milled from the smaller fractional segments.

Minor software programming changes may be provided at this point so that existing CNC milling devices can receive the modified shapes and sizes for final milling.

At this stage of processing, the endosperm is milled with the aid of a computer processor to fashion a particular patient's denture, or other prosthetic, by applying patient specific data such as jaw shape and size dimensions; together with the desired structural and cosmetic aspects of the final prosthetic to be milled.

In the preferred embodiment, dentists provide the data about the patient specific denture dimensional requirements together with cosmetic specifications to the milling facility over a network such as the Internet. The computer assisted milling of the pre-formed Tagua segments into the dental prothesis is then completed at the facility and shipped to the dentist or customer. Alternatively, the milling step can be done right at the dentist's office if suitable equipment is present there.

Data about the patient's mouth may be measured using manual or computer assisted means such as a scanning device. Alternatively, the data can be derived by other imaging methods like an MRI. However measured, the specific individual patient data is provided to a CNC Milling Machine such as a CEREC Device and a customized final dental prosthetic, as illustrated in FIG. 5 is fashioned by computer assistance.

This method leverages the natural size and curvature of the tagua nut which approximates to the general arc size, curvature, and quasi-bowl shape of the human jaw and palette. The method minimizes processing and resulting energy use in the production of the prosthetic. Moreover, the tagua material is an entirely natural renewable resource that is of sufficient hardness and impermeability for ready use as denture material after appropriate treatment.

After the final prosthetic has been carved in accordance with the particular patient's data, additional qualities may be provided to the Tagua material by use of natural biocompatible means and materials. For example, naturally produced mussel or barnacle adhesive may be used to add hydroxyapatite as an enamel. This material may be added to provide additional degrees of hardness and insolubility. Such additional qualities may be desirable when the prosthesis is to be permanently fixed to dental implants. Any other biocompatible means of adding additional qualities to the tagua can also be used. A dopamine solution can be used to adhere hydroxyapatite or other natural minerals or material.

In the preferred embodiment, the carved Tagua material is dipped directly into an aqueous dopamine solution at pH 8.5. Autopolymerization occurs and the taugua substrate is thereby coated with a polydopamine film up to 50 nm thick. The polydopamine film is surface-active and readily adheres to hydroxyapatite which is then provided for coating the treated tagua by either direct addition of the mineral to the surface or by precipitation out of a solution, such as simulated body fluid.

Additional steps may be performed to regulate the formation of the hydroxyapatite enamel coating which include the placing the protein amelogenin in the solution with hydroxyapatite which regulates the initiation and growth of hydroxyapatite crystals during the mineralization of the enamel.

Temporary caps that are to be mounted on impaired teeth may be rendered with or without additional treatment of the milled Tagua prosthesis.

The steps included here can be altered, and various modifications can be made to the method without departing from the scope of the invention. There are a variety of ways that the natural qualities of size and shape of the Tagua nut can be leveraged by preforming and treating to enhance the economic use of the material without departing from the scope of this invention. The nuts can be fractionally cut into a variety of to be standardized units that meet the demands of single caps, bridges, partial, or full denture sets. The embodiment outlined herein is just one example of how the natural qualities of the Tagua material can be economically and efficiently modified to create a dental prosthesis in a way that is sustainable, biocompatible, and without significant waste.

The invention claimed is:
1. A method of manufacturing a dental device, the method comprising:
dehydrating an endosperm of a tree nut;
cutting the endosperm into a shape and size configured to be milled by a computer aided milling device;
milling the endosperm into a milled piece of tree nut having a shape configured to replace at least a portion of a tooth of an individual; and treating the milled piece of tree nut with an aqueous solution resulting in an enameled tooth surface comprising hydroxyapatite.

2. The method of claim 1, wherein the aqueous solution comprises a dopamine based adhesive.

3. The method of claim 1, wherein the dental device is a replacement tooth, a crown, a cap, a bridge, at least a part of a denture, or a denture.

4. The method of claim 2, wherein a mussel or barnacle adhesive is used when treating the milled piece of tree nut with the aqueous solution.

5. The method of claim 2, wherein the aqueous solution is at a pH of about 8.5.

6. The method of claim 1, wherein cutting the endosperm into the shape and size configured to be milled by the computer aided milling device comprises:
cutting the endosperm into at least one hemisphere; and
cutting at least one segment from the hemisphere.

7. The method of claim 6, further comprising boring a central portion of the at least one hemisphere, wherein a boring bit with a rounded tip is used for boring the central portion, wherein the boring passes through a surface of the at least one hemisphere, the boring configured to shape the at least one hemisphere into a bowl-shaped ring.

8. The method of claim 1, further comprising matching a color of the dental device to a color of one or more teeth of the individual, wherein the matching includes bleaching the tree nut.

9. The method of claim 1, wherein the tree nut is a Tagua nut.

10. The method of claim 1, wherein the cutting step comprises cutting the endosperm into at least one segment to expose a hollow center area of the endosperm and then cutting the least one segment into at least one additional segment.

11. The method of claim 1, wherein the cutting step comprises cutting the endosperm into at least one segment to expose a hollow center area of the endosperm; and further comprising boring the hollow center area of the endosperm to provide a surface thereon with no crevices.

12. The method of claim 1, wherein treating step comprises coating the milled piece of tree nut with a polydopamine film.

13. The method of claim 12, wherein the treating step further comprises applying a solution to the dopamine film on the milled piece of tree nut and precipitating hydroxyapatite out of the solution onto the dopamine film.

14. The method of claim 12, wherein the treating step further comprises directly applying hydroxyapate mineral to the dopamine film on the milled piece of tree nut.

15. The method of claim 13, wherein the solution further comprises amelogenin protein.

* * * * *